United States Patent [19]

Koga et al.

[11] Patent Number: 5,420,352

[45] Date of Patent: May 30, 1995

[54] PROCESS FOR THE PRODUCTION OF 1-PHENOXY-2-AMINOPROPANE

[75] Inventors: Hidetoshi Koga; Izumi Terada, both of Sodegaura, Japan

[73] Assignee: Idemitsu Kosan Co., Ltd., Tokyo, Japan

[21] Appl. No.: 244,527

[22] Filed: May 31, 1994

[30] Foreign Application Priority Data

Oct. 19, 1992 [JP] Japan .................. 4-280084

[51] Int. Cl.$^6$ .................. C07C 209/16
[52] U.S. Cl. .................. 564/353
[58] Field of Search .................. 564/353

[56] References Cited

U.S. PATENT DOCUMENTS 5,286,905  2/1994  Nakamura .

FOREIGN PATENT DOCUMENTS 63-264465 11/1988 Japan .
4-334355 11/1992 Japan .
142711 11/1988 Poland .

OTHER PUBLICATIONS

E. J. Kaniewska et al, "Catalytic Amination of Alcohols", (1988), pp. 387–393, *Stud. Surf. Sci, Catal.*
Chemical Abstracts, 111(16): 136425k (1989).

Chemical Abstracts, 109(26): 233141f (1988).

*Primary Examiner*—Richard L. Raymond
*Attorney, Agent, or Firm*—Frishauf, Holtz, Goodman & Woodward

[57] ABSTRACT

1-Methyl-2-phenoxy ethanol of the formula,

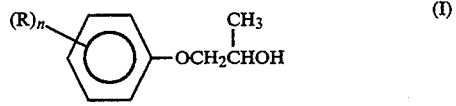

(I)

[wherein R is hydrogen or an alkyl group having 1 to 6 carbon atoms, and n is an integer of 0 or 1 to 5]

is allowed to react with ammonia in a solvent in the presence of a copper-chromium catalyst and hydrogen, whereby 1-phenoxy-2-aminopropane of the formula

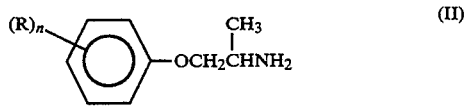

(II)

[wherein R and n are as defined above] can be obtained at high yields at high selectivity.

18 Claims, No Drawings

PROCESS FOR THE PRODUCTION OF 1-PHENOXY-2-AMINOPROPANE

TECHNICAL FIELD

This application is a 371 of PCT/JP93/01499, filed Oct. 19, 1993.

The present invention relates to a process for the production of 1-phenoxy-2-aminopropane useful as an intermediate for triazine herbicides.

TECHNICAL BACKGROUND

As a triazine herbicide, JP-A-63-264465 discloses a triazine herbicide in which a (3,5-dimethylphenoxy)-alkylamino group is substituted on a triazine ring, as is represented by the formula,

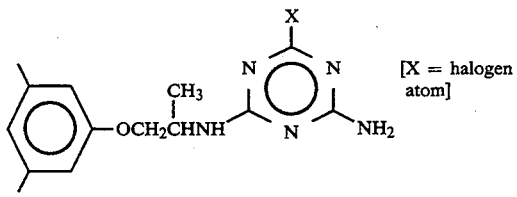

[X = halogen atom]

The above Japanese Publication describes that the above triazine herbicide has remarkable advantages in that it is not only excellent in herbicidal activity but also free of phytotoxicity to paddy rice.

According to the above Publication, the above (3,5-dimethylphenoxy)alkylamino group-substituted triazine herbicide is obtained by reacting 1-(3,5-dimethylphenoxy)-2-aminopropane with 2-amino-4,6-dihalotriazine. It is also described that the 1-(3,5-dimethylphenoxy)-2-aminopropane used in the above reaction is obtained by reacting (3,5-dimethylphenoxy)acetone with sodium cyanoborohydride in methanol in the presence of ammonium acetate (this process will be referred to as Conventional Process I). Conventional Process I is represented by the following scheme.

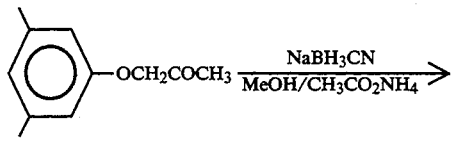

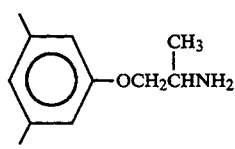

However, the defect with the above Conventional Process I is that the yield of 1-(3,5-dimethylphenoxy)-2-aminopropane as the intended compound is very low, as low as about 30%.

Meanwhile, as a process for the production of 1-(2,6-dimethylphenoxy)-2-aminopropane which is a structural isomer of 1-(3,5-dimethylphenoxy)-2-aminopropane, Polish Laid-open Patent Publication No. 142711 discloses a process in which 1-methyl-2-(2,6-dimethylphenoxy)ethanol is reacted with ammonia in the presence of a copper-nickel catalyst and hydrogen, as is shown in the following scheme (this process will be referred to as Conventional Process 2).

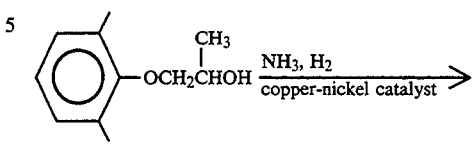

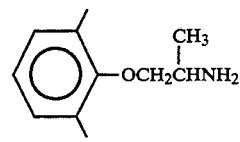

However, the defect with Conventional Process 2 is that since a large amount of 2,6-xylenol is formed as a byproduct in addition to 1-(2,6-dimethylphenoxy)-2-aminopropane, the selectivity to the intended compound is low. For example, in Example 6 of the above Polish Publication, the byproduct (2,6-xylenol) is formed in an amount of as much as 25% and the yield of the intended compound is 58%, so that the selectivity to the intended compound is as low as 70%.

As explained above, there has been known no process in which 1-phenoxy-2-aminopropane can be obtained at high yields at high selectivity, and it has been desired to develop a process therefor.

DISCLOSURE OF THE INVENTION

It is therefore an object of the present invention to provide a process for the production of 1-phenoxy-2-aminopropane at high yields at high selectivity.

The present inventors have made studies to achieve the above object, and as are result, have found that 1-methyl-2-phenoxy ethanol of the formula,

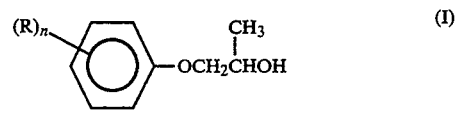

[wherein R is hydrogen or an alkyl group having 1 to 6 carbon atoms, and n is an integer of 0 or 1 to 5] is allowed to react with ammonia in a solvent in the presence of a copper-chromium catalyst and hydrogen, whereby the formation of a lower alkyl-substituted phenol is inhibited and 1-phenoxy-2-aminopropane of the formula

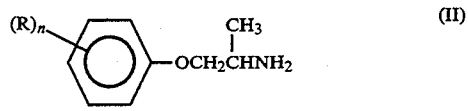

[wherein R and n are as defined above] can be obtained at high yields at high selectivity. On the basis of this finding, the present invention has been completed.

The gist of the present invention therefore consists in a process for the production of 1-phenoxy-2-aminopropane of the above formula (II), which comprises reacting 1-methyl-2-phenoxyethanol of the above formula (I) with ammonia in a solvent in the presence of a copper-chromium catalyst and hydrogen.

PREFERRED EMBODIMENTS OF THE INVENTION

The present invention will be detailed hereinafter.

In the compound of the formula (I) used as a starting compound in the present invention, R is hydrogen or an alkyl group having 1 to 6 carbon atoms such as methyl, ethyl, propyl, butyl, pentyl or hexyl. R is preferably hydrogen or an alkyl group having 1 to 4 carbon atoms. n is an integer of 0 or 1 to 5. When n is 0, it means that no alkyl group is substituted on the phenyl group. When n is 1 to 5, it means that 1 to 5 alkyl groups are substituted on the phenyl group. The starting compound represented by the formula (I) is particularly preferably 1-methyl-2-(3,5-dimethylphenoxy)ethanol of the formula.

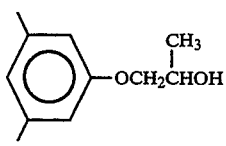

(Ia)

In the present invention, 1-methyl-2-phenoxyethanol is reacted with ammonia whereby the intended compound, 1-phenoxy-2-aminopropane of the formula (II), is obtained. The molar ratio of ammonia to the starting compound (I) is preferably 1.0 to 10.0. The reasons therefor are as follows. When the ammonia/starting compound molar ratio is less than 1.0, the amount of the ammonia based on the starting compound (I) is short of a stoichiometric amount and the yield of the intended compound (II) is low. When the ammonia/starting compound (I) molar ratio exceeds 10.0, no further improvement in yields can be expected. The ammonia/starting compound (I) molar ratio is particularly preferably 1.2 to 4.0. That is, for obtaining the intended compound (II) by reacting the starting compound (I) with ammonia, it is preferred to feed a predetermined excess amount of ammonia relative to the starting compound (I).

In the present invention, the above reaction between the starting compound (I) and ammonia uses a copper-chrominum catalyst as a catalyst. As the copper-chromium catalyst, preferred is a catalyst which contains copper and chromium in the form of an oxide each in amounts as required and optionally contains manganese and barium in the form of oxide each in amounts as required, and which has a chemical composition of CuO: 30–50%, $Cr_2O_3$: 30–50%, $MnO_x$ (x=1 or 2): 0–10% and BaO: 0–15%. In particular, the content of CuO is preferably 40–50%, the content of $Cr_2O_3$ is preferably 40–50%, the content of $MnO_x$ (x=1 or 2) is preferably 2–8%, and the content of BaO is preferably 0–10%. Specific examples of the above copper-chromium catalyst include N203 and N203 S supplied by Nikki Chemical Co., Ltd., G99c supplied by Nissan Girdler Catalyst Co., Ltd., Cu-1106P and Cu-1160P supplied by Engelhard Corporation and C-5A supplied by Sakai Chemical Industry Co., Ltd. The weight ratio of the copper-chromium catalyst to the starting compound (I) is preferably 0.025 to 1.0. The reasons therefor are as follows. When the catalyst/starting compound (I) weight ratio is less than 0.025, the yield and selectivity are not yet sufficient although they are improved over the above Conventional Processes 1 and 2. When the catalyst/starting compound (I) weight ratio exceeds 1.0, no further improvements in the yield and selectivity can be expected. The catalyst/starting compound (I) weight ratio is particularly preferably 0.05 to 0.3. The above copper-chromium catalyst may be a product prepared by supporting them on carrier such as silica or alumina.

In the present invention, for further improving the yield of the intended compound, a cocatalyst may be used together with the above copper-chromium catalyst as required. The cocatalyst can be selected from metal catalysts containing noble metals such as nickel, cobalt, palladium and platinum, which are hydrogenation catalysts, a stabilized nickel catalyst and a ruthenium catalyst in which ruthenium is supported on a carbon carrier, while it is particularly preferred to use N-103 (having an Ni+NiO content of 49 to 52% and containing diatomaceous earth and graphite as a carrier) supplied by Nikki Chemical Co., Ltd. The noble metal preferably includes metals coming under the periodic table Group VIII.

The cocatalyst/starting compound (I) weight ratio is preferably 0.001 to 0.05, particularly preferably 0.001 to 0.01.

In the present invention, the reaction is carried out in hydrogen-containing atmosphere, and the reaction pressure in this case is preferably set at 1 to 200 kg/cm$^2$G. The reasons therefor are as follows. When the reaction pressure is less than 1 kg/cm$^2$G, the yield of the intended compound decreases. When it exceeds 200 kg/cm$^2$G, the yield is not any further improved. The reaction pressure is particularly preferably 60 to 170 kg/cm$^2$G. As the reaction proceeds, the reaction pressure decreases. The reaction pressure may be kept at a predetermined level by feeding hydrogen during the reaction, or it may be left to take its own course as it goes.

In the present invention, it is essential to carry out the reaction in a solvent for obtaining the intended compound of the formula (II) from the starting compound of the formula (I). According to the present invention, the intended compound of the formula (II) is formed from the starting compound (I) of the formula (II) at high yields at high selectivity as described above, while the formation of the intended compound of the formula (II) at high yields at high selectivity are greatly attributed to carrying out the above reaction in a solvent. This point will be apparent when the yield and selectivity in Examples using a solvent and those in Comparative Examples using no solvent, which will be described later, are compared.

As the solvent used in the present invention, preferred are aliphatic hydrocarbons, aromatic hydrocarbons or polycyclic aromatic hydrocarbons. Specific examples of the aliphatic hydrocarbons include aliphatic hydrocarbons having 3 to 12 carbon atoms such as propane, butane, pentane, hexane, heptane, octane, nonane, decane, undecane and dodecane. Specific examples of the aromatic hydrocarbons include aromatic hydrocarbons having 6 to 20 carbon atoms such as benzene and alkyl-substituted benzenes such as toluene, mesitylene, xylene, ethylbenzene and isopropylbenzene. Examples of the fused-ring aromatic hydrocarbons include polycyclic hydrocarbons having 10 to 20 carbon atoms such as naphthalene, alkyl-substituted naphthalene, tetralin, alkyl-substituted tetralin and diphenyl. The alkyl substituents above preferably have 1 to 10 carbon atoms.

The solvent is preferably used in such an amount that the solvent/starting compound (I) weight ratio is 0.5 to 18. The reasons therefor are as follows. When the above weight ratio is less than 0.5, the amount of the solvent is too small, and the solvent scarcely has an effect. When it exceeds 18, the amount of the solvent is too large, and the reaction and post-treatment procedures are made inefficient. The solvent/starting compound (I) weight ratio is particularly preferably 1 to 2.

In the present invention, the starting compound (1-methyl-2-phenoxyethanol), the catalyst, the solvent and ammonia are charged, for example, by any one of the following methods.

(1) The starting compound, the catalyst and the solvent are charged into a pressure vessel, and ammonia is further added. Then, the pressure in the reaction vessel is increased by applying hydrogen pressure as will be described later.

(2) The catalyst, ammonia and the solvent are charged into a pressure vessel and the temperature is increased. Then, the starting compound and the catalyst are charged, and then hydrogen pressure is applied to increase the pressure.

(3) Ammonia and the solvent are charged into a pressure vessel, and while the pressure in the pressure vessel is increased by applying hydrogen pressure, the temperature of the mixture is increased. Then, the starting compound and the catalyst are charged, and the pressure is further increased by applying hydrogen pressure.

(4) The solvent and ammonia are charged into a pressure vessel, and while the pressure in the pressure vessel is increased by applying hydrogen pressure, the temperature of the mixture is increased. Then, the starting compound and the catalyst are charged.

At any step in any one of the above methods (1) to (4), the cocatalyst may be added.

Further, in the present invention, after the reaction system containing the starting compound, the solvent and ammonia reach an intended reaction temperature, the catalyst and optionally the cocatalyst may be added, whereby a side reaction at a low temperature can be prevented.

Further, according to the present invention, the copper-chromium catalyst may be divided into portions to add the portions separately from each other during the reaction. This addition of portions of the catalyst provides advantages that the catalyst can be fed to make up for the deficiency of the catalyst while inhibiting a side reaction and observing the progress in the reaction, that the reaction conversion can be improved, and the reaction time can be decreased, whereby the formation of dimers and xylenol can be inhibited. Further, the cocatalyst may be also divided into portions to add the portions separately from each other.

In the present invention, the reaction temperature and the reaction time are not critical, while the reaction temperature is preferably 150° to 300° C., particularly preferably 200° to 270° C. Although depending upon the reaction temperature, the reaction time is preferably 2 to 30 hours, particularly preferably 2 to 15 hours.

According to the process for the production of 1-phenoxy-2-aminopropane (II), provided by the present invention, ammonia is reacted with 1-methyl-2-phenoxyethanol (I) in the solvent in the presence of the copper-chromium catalyst and hydrogen, whereby 1-phenoxy-2-aminopropane (II) can be obtained at high yields at high selectivity. There are therefore advantages in that not only it is easy to isolate and purify the intended compound, but also it is easy to recover unreacted starting compound.

The present invention will be further explained hereinafter with reference to Examples.

EXAMPLE 1

A 150 cc autoclave was charged with 30.0 g (166 mmol) of 1-methyl-2-(3,5-dimethylphenoxy)ethanol, 3.0 g of a copper-chromium catalyst (N203SD, supplied by Nikki Chemical Co., Ltd.: CuO 44%, $Cr_2O_3$ 44%, $MnO_2$ 5G %) and 30.0 g of a solvent (toluene). Further, 9.6 g (564 mmol) of ammonia was added, a hydrogen pressure of 40 kg/cm$^2$G was applied, and then the temperature of the mixture was increased up to 240° C. The mixture was stirred at a reaction pressure of 104 to 97 kg/cm$^2$G for 7 hours. The reaction mixture was allowed to cool, and the pressure of an excess of ammonia and hydrogen was released. Then, the catalyst was removed by filtration. The resultant filtrate was extracted with 100 ml of a 20% hydrochloric acid aqueous solution. The extracted aqueous layer was neutralized with a 20% sodium hydroxide aqueous solution, and 200 ml of ethyl ether was added to the aqueous layer for extraction. The organic layer was dried over anhydrous sodium sulfate, and then the solvent was distilled off under reduced pressure to give 15.2 g of the intended compound, 1-(3,5-dimethylphenoxy)-2-aminopropane (yield 51%). The selectivity to the intended compound, calculated on the basis of the total amount of the starting compound, was 81%.

EXAMPLES 2–10

The procedures in Example 1 were repeated except that the reaction conditions were changed as shown in Table 1. Table 1 shows the yields of, and selectivity to, intended products together with the results of Example 1.

COMPARATIVE EXAMPLE 1

The procedures in Example 1 were repeated except that 30.0 g of toluene was not used and that $H_2$ was charged to set the reaction pressure at 136 to 123 kg/cm$^2$G. Table 1 shows the yield of, and the selectivity to, the intended compound.

COMPARATIVE EXAMPLE 2

The procedures of Example 1 were repeated except that 30.0 g of toluene was not used and that N-103 was used as a cocatalyst. Table 1 shows the yield of, and the selectivity to, the intended compound.

TABLE 1

| | | (No. 1) | | | |
|---|---|---|---|---|---|
| Ex. No. | Solvent (g) | Copper-chromium catalyst (g) | Co-catalyst (g) | $NH_3$ amount (g) | Reaction pressure (kg/cm$^2$G) |
| 1 | toluene 30.0 | N-203SD(5) 3.0 | — | 9.6 | 110–106 |
| 2 | KSK-oil(4) 30.0 | N-203SD 3.0 | — | 9.6 | 80–76 |
| 3 | toluene 30.0 | N-203SD 3.0 | N-103(8) 0.09 | 6.8 | 106–103 |
| 4 | toluene 30.0 | N-203SD 3.0 | Ru/C(9) 0.15 | 4.8 | 77–68 |
| 5 | toluene 30.0 | N-203 3.0 | N-103 0.15 | 6.8 | 100–89 |
| 6 | toluene 30.0 | G-99C(7) 3.0 | N-103 0.15 | 6.8 | 99–88 |
| Ex. | | Yields (%) | | | Selectivity |

TABLE 1-continued

| No. | PhO—C$_3$—NH$_2$(1) | PhOH(2) | dim(3) | (%) |
|---|---|---|---|---|
| 1 | 52 | 4 | 9 | 81 |
| 2 | 66 | 8 | 15 | 74 |
| 3 | 73 | 8 | 9 | 81 |
| 4 | 63 | 7 | 13 | 76 |
| 5 | 71 | 9 | 5 | 84 |
| 6 | 73 | 7 | 5 | 85 |

(No. 2)

| Ex. No. | Solvent (g) | Copper-chromium catalyst (g) | Co-catalyst (g) | NH$_3$ amount (g) | Reaction pressure (kg/cm$^2$G) |
|---|---|---|---|---|---|
| 7 | tetralin 19.8 | N-203SD(5) 1.98 | — | 6.2 | 155–148 |
| 8 | toluene 30.0 | G-99C(7) 3.0 | N-103(8) 0.15 | 7.4 | 118–108 |
| 9 | toluene 30.0 | G-99C 3.0 | — | 6.8 | 127–108 |
| 10 | toluene 30.0 | C-5A(10) 3.0 | N-103 0.15 | 7.4 | 101–81 |
| CEx. | | | | | |
| 1 | — | N-203SD 3.0 | — | 9.6 | 136–123 |
| 2 | — | N-203SD 3.0 | N-103 0.15 | 4.8 | 106–80 |

| Ex. No. | Yields (%) PhO—C$_3$—NH$_2$(1) | PhOH(2) | dim(3) | Selectivity (%) |
|---|---|---|---|---|
| 7 | 77 | 4 | 8 | 84 |
| 8 | 75 | 6 | 4 | 88 |
| 9 | 68 | 5 | 12 | 79 |
| 10 | 73 | 10 | 6 | 82 |
| CEx. | | | | |
| 1 | 39 | 7 | 16 | 59 |
| 2 | 16 | 27 | 0 | 37 |

Ex. No. = Example No., CEx. = Comparative Example
(1) PhO—C$_3$—NH$_2$: intended amine (1-phenoxy-2-aminopropane)
(2) PhOH: 3,5-xylenol
(3) dim: dimer
(4) KSK-oil 280: alkylnaphthalene supplied by Soken Chemical & Engineering Co., Ltd.
(5) N-203SD: composition of 44% CuO, 44% Cr$_2$O$_3$ and 5% MnO$_2$, supplied by Nikki Chemical Co., Ltd.
(6) N-203: composition of 44% CuO, 44% Cr$_2$O$_3$ and 5% MnO$_2$, supplied by Nikki Chemical Co., Ltd.
(7) G-99C: composition of 36% Cu, 32% Cr, 2% Mn, 2% Mn and 2% Ba, supplied by Nissan Girdler Catalyst Co., Ltd.
(8) N-103: containing 49–52% Ni + NiO, diatomaceous earth and graphite as a carrier supplied by Nikki Chemical Co., Ltd.
(9) Ru/C: containing 10% Ru, supplied by Aldrich Chemical Company, Inc.
(10) C-5A: composition of 48% CuO, 44% Cr$_2$O$_3$ and 4% MnO, supplied by Sakai Chemical Industry Co., Ltd.

Table 1 shows that the intended compound, 1-phenoxy-2-aminopropane, was obtained at high yields at high selectivity in Examples 2 to 10 as well as it was obtained in Example 1. In contrast, in Comparative Examples 1 and 2 using no solvent, both the yields of the intended compound and the selectivity thereto were particularly low.

EXAMPLE 11

A 150 cc autoclave was charged with 2.63 g of a copper-chromium catalyst (C-5A, supplied by Sakai chemical Industry Co., Ltd.: CuO 48%, Cr$_2$O$_3$ 44%, MnO 4%), 11.79 g (692 mmol) of ammonia and 37.5 g of a solvent (toluene), and the mixture was temperature-increased up to 240° C. Then, 37.5 g (208 mmol) of 1-methyl-2-(3,5-dimethylphenoxy)ethanol of the formula (Ia), 3.75 g of a copper-chromium catalyst (the same as the above C-5A supplied by Sakai Chemical Industry Co.) and 0.16 g of a cocatalyst (N-103, supplied by Nikki Chemical Co., Ltd.: (Ni+NiO) 49–52%) were heated up to 70°–100° C. and charged into the autoclave. Then, the reaction pressure was elevated to 120 kg/cm$^2$G with hydrogen pressure, and the mixture was stirred for 3 hours. After 3 hours, 2.63 g of a copper-chromium catalyst (the same as the above C-5A supplied by Sakai Chemical Industry Co., Ltd.) and 0.11 g of a cocatalyst (the same as the above N-103 supplied by Nikki Chemical Co., Ltd.) were charged into the autoclave, and the mixture was stirred at 240° C. for 6.5 hours.

After the reaction mixture was allowed to cool, and the pressure of an excess of ammonia and hydrogen was released. Then, the catalyst was removed by filtration. The resultant filtrate was extracted with 100 ml of a 20% hydrochloric acid aqueous solution. The extracted aqueous layer was neutralized with a 20% sodium hydroxide aqueous solution, and 200 ml of ethyl ether was added to the aqueous layer for extraction.

The organic layer was dried over anhydrous sodium sulfate, and then the solvent was distilled off under reduced pressure to give 28.6 g of the intended compound, 1-(3,5-dimethylphenoxy)-2-aminopropane (yield 77%). The selectivity to the intended compound, calculated on the basis of the total amount of the starting compound, was 83%.

EXAMPLE 12

A 150 cc autoclave was charged with 0.05 g of a cocatalyst (N-103, supplied by Nikki Chemical Co., Ltd.) and 37.5 g of a solvent (toluene), and further charged with 10.7 g (629 mmol) of ammonia. A hydrogen pressure of 20 kg/cm$^2$G was applied, and the temperature of the mixture was increased up to 240° C. Then, 37.5 g (208 mmol) of 1-methyl-2-(3,5-dimethylphenoxy)ethanol of the formula (Ia) and 3.75 g of a copper-chromium catalyst (C-5A, supplied by Sakai Chemical Industry Co., Ltd.) were heated up to 70° to 100° C. and charged into the autoclave.

Then, the reaction pressure was elevated up to 120 kg/cm$^2$ with hydrogen pressure, and the mixture was stirred for 4.5 hours.

The same post treatment as that in Example 11 was carried out to give 28.1 g of the intended compound, 1-(3,5-dimethylphenoxy)-2-aminopropane (yield 75%). The selectivity to the intended compound was 82%.

EXAMPLE 13

A 150 cc autoclave was charged with 13.4 g (788 mmol) of ammonia and 37.5 g of a solvent (toluene), and a hydrogen pressure of 20 kg/cm$^2$G was applied and the temperature of the mixture was elevated up to 240° C. Then, 37.5 g (208 mmol) of 1-methyl-2-(3,5-dimethylphenoxy)ethanol of the formula (Ia), 5.63 g of a copper-chromium catalyst (C-5A, supplied by Sakai Chemical Industry Co., Ltd.) and 0.27 g of a cocatalyst (N-103, supplied by Nikki Chemical Co., Ltd.) were heated up to 70° to 100° C. and charged into the autoclave.

Then, the reaction pressure was elevated up to 120 kg/cm$^2$G with hydrogen pressure, and the mixture was stirred for 6.5 hours.

The same post treatment as that in Example 11 was carried out to give 27.3 g of the intended compound, 1-(3,5-dimethylphenoxy)-2-aminopropane (yield 73%). The selectivity to the intended compound was 77%.

EXAMPLES 14 AND 15

The procedures of Example 13 were repeated except that the reaction conditions were changed as shown in Table 2.

Table 2 shows the yields of, and the selectivity to, the intended compound together with the results obtained in Examples 11 to 13.

TABLE 2

| Ex. No. | Solvent (g) | Copper-chromium catalyst (g) | Cocatalyst (g) | NH3 amount (g) | Reaction pressure (kg/cm²G) |
|---|---|---|---|---|---|
| 11 | toluene 37.5 | C-5A(10) 2.63 + 3.75 + 2.63 | N-103(8) 0 + 0.16 + 0.11 | 11.79 | 120 |
| 12 | toluene 37.5 | C-5A 0 + 3.75 | N-103 0.05 + 0 | 10.7 | 120 |
| 13 | toluene 37.5 | C-5A 5.63 | N-103 0.27 | 13.4 | 120 |
| 14 | toluene 37.5 | C-5A 3.75 | N-103 0.11 | 9.14 | 120 |
| 15 | toluene 37.5 | C-5A 3.75 | N-103 0.05 | 10.74 | 120 |

| Ex. | Reaction time | Yields (%) PhO—C3—NH2(1) | PhOH(2) | dim(3) | Selectivity (%) |
|---|---|---|---|---|---|
| 11 | 0 + 3 + 6.5 | 77 | 8 | 2 | 83 |
| 12 | 0 + 4.5 | 75 | 7 | 7 | 82 |
| 13 | 6.5 | 73 | 17 | 2 | 77 |
| 14 | 4 | 70 | 11 | 9 | 75 |
| 15 | 4.5 | 73 | 12 | 7 | 77 |

Ex. No. = Example No.
(1) PhO—C3—NH2: intended amine (1-phenoxy-2-aminopropane)
(2) PhOH: 3,5-xylenol
(3) dim: dimer
(8) N-103: containing 49–52% (Ni + NiO), diatomaceous earth and graphite as a carrier supplied by Nikki Chemical Co., Ltd.
(10) C-5A: composition of 48% CuO, 44% Cr2O3, and 4% MnO, supplied by Sakai Chemical Industry Co., Ltd.

Table 2 shows that the intended compound, 1-phenoxy-2-aminopropane, was obtained at high yields at high selectivity in Examples 14 and 15 as well as it was obtained in Examples 11 to 13.

What is claimed is:

1. A process for the production of 1-phenoxy-2-aminopropane of the formula (II),

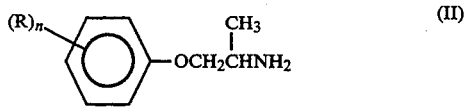

wherein R is hydrogen or an alkyl group having 1 to 6 carbon atoms and n is an integer of 0 or 1 to 5, which comprises reacting 1-methyl-2-phenoxyethanol of the formula (I)

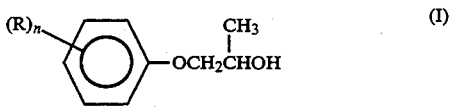

wherein R is as defined above,
with ammonia in a solvent in the presence of a copper-chromium catalyst and hydrogen.

2. The process of claim 1, wherein the solvent is an aliphatic hydrocarbon, an aromatic hydrocarbon or a polycyclic aromatic hydrocarbon.

3. The process of claim 1, wherein the catalyst is fed after an intended reaction temperature is achieved.

4. The process of claim 1, wherein the copper-chromium catalyst is divided into portions and the portions are added separately from each other.

5. The process of claim 1, wherein R is an alkyl group having 1 to 4 carbon atoms.

6. The process of claim 1, wherein a molar ratio of the ammonia to the 1-methyl-2-phenoxyethanol is 1.0 to 10.0.

7. The process of claim 6, wherein the molar ratio of the ammonia to the 1-methyl-2-phenoxyethanol is 1.2 to 4.0.

8. The process of claim 1, wherein the copper-chromium catalyst has a composition of CuO: 30 to 50%, Cr2O3: 30 to 50%, MnOx: 0 to 10%, wherein x is 1 or 2, BaO: 0 to 15%.

9. The process of claim 8, wherein the copper-chromium catalyst has a composition of CuO: 40 to 50%, Cr2O3: 40 to 50%; MnOx: 0 to 10% and BaO: 0 to 15%.

10. The process of claim 6, wherein a weight ratio of the copper-chromium catalyst to the 1-methyl-2-phenoxyethanol is 0.025 to 1.0.

11. The process of claim 10, wherein the weight ratio of the copper-chromium catalyst to the 1-methyl-2-phenoxyethanol is 0.05 to 0.3.

12. The process of claim 1, which further comprises carrying out the reaction in the presence of a cocatalyst, said cocatalyst containing a metal selected from the group consisting of nickel, cobalt, palladium, platinum and ruthenium, wherein a weight ratio of the cocatalyst to the 1-methyl-2-phenoxyethanol is 0.001 to 0.05.

13. The process according to claim 10, wherein the process is carried out at a pressure of 1 to 200 kg/cm²G.

14. The process according to claim 13, wherein the pressure is 60 to 170 kg/cm²G.

15. The process according to claim 13, wherein the solvent is selected from the group consisting of propane, butane, pentane, hexane, heptane, octane, nonane, decane, undecane, dodecane, benzene, toluene, mesitylene, xylene, ethylbenzene, isopropylbenzene, naphthalene and tetralin; and a weight ratio of the solvent to the 1-methyl-2-phenoxyethanol is 0.5 to 18.

16. The process according to claim 15, wherein the process is carried out at a temperature of 150° to 300° C. for a time of 2 to 30 hours.

17. The process according to claim 16, wherein the temperature is 200° to 270° C. and the time is 2 to 15 hours.

18. The process according to claim 17, wherein the 1-methyl-2-phenoxyethanol is 1-methyl-2-(3,5-dimethylphenoxy) ethanol.

* * * * *

UNITED STATES PATENT AND TRADEMARK OFFICE
CERTIFICATE OF CORRECTION

PATENT NO. : 5,420,352
DATED : May 30, 1995
INVENTOR(S) : Koga et al

It is certified that error appears in the above-indentified patent and that said Letters Patent is hereby corrected as shown below:

Title page, left column, the line starting with "[22]" should be replaced by the following:

--[22]  PCT Filed:        Oct. 19, 1993
      [86]  PCT No.:          PCT/JP93/01499
            § 371 Date:       May 31, 1994
            § 102(e) Date:    May 31, 1994
      [87]  PCT Pub. No.:     WO 94/08944
            PCT Pub. Date:    Apr. 28, 1994--.

Signed and Sealed this

Eleventh Day of June, 1996

Attest:

BRUCE LEHMAN

*Attesting Officer*      Commissioner of Patents and Trademarks